(12) United States Patent
Soltis et al.

(10) Patent No.: US 11,541,245 B2
(45) Date of Patent: *Jan. 3, 2023

(54) DELIVERY DEVICES AND METHODS FOR LEADLESS CARDIAC DEVICES

(71) Applicant: CARDIAC PACEMAKERS, INC., St. Paul, MN (US)

(72) Inventors: Brian Soltis, St. Paul, MN (US); Benjamin J. Haasl, Forest Lake, MN (US); James P. Goodman, Shorewood, MN (US); Vincent P. Hackenmueller, Elk River, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 172 days.

This patent is subject to a terminal disclaimer.

(21) Appl. No.: 16/988,847

(22) Filed: Aug. 10, 2020

(65) Prior Publication Data

US 2020/0368539 A1 Nov. 26, 2020

Related U.S. Application Data

(63) Continuation of application No. 15/879,937, filed on Jan. 25, 2018, now Pat. No. 10,773,089.
(Continued)

(51) Int. Cl.
*A61N 1/37* (2006.01)
*A61N 1/375* (2006.01)
(Continued)

(52) U.S. Cl.
CPC ........ *A61N 1/3756* (2013.01); *A61B 17/3468* (2013.01); *A61M 25/0074* (2013.01);
(Continued)

(58) Field of Classification Search
CPC .......................... A61N 1/3756; A61N 1/37512
(Continued)

(56) References Cited

U.S. PATENT DOCUMENTS

| 4,301,815 A | 11/1981 | Doring |
| 5,807,399 A | 9/1998 | Laske et al. |

(Continued)

FOREIGN PATENT DOCUMENTS

| EP | 2818201 B1 | 7/2016 |
| EP | 2658599 B1 | 10/2016 |

(Continued)

OTHER PUBLICATIONS

International Search Report and Written Opinion dated Aug. 16, 2018 for International Application No. PCT/US2018/015226.

*Primary Examiner* — Nicole F Lavert
(74) *Attorney, Agent, or Firm* — Seager, Tufte & Wickhem LLP

(57) ABSTRACT

Delivery devices, systems, and methods for delivering implantable leadless pacing devices are disclosed. An example delivery device may include an intermediate tubular member and an inner tubular member slidably disposed within a lumen of the intermediate tubular member. A distal holding section may extend distally of a distal end of the intermediate tubular member and define a cavity therein for receiving an implantable leadless pacing device. The device may be configured to enable fluid flushing of the delivery device prior to use, to remove any air from within the device as well as providing the option of fluid flow during use of the delivery device.

20 Claims, 19 Drawing Sheets

Related U.S. Application Data

(60) Provisional application No. 62/450,727, filed on Jan. 26, 2017.

(51) Int. Cl.
*A61N 1/05* (2006.01)
*A61M 25/00* (2006.01)
*A61N 1/372* (2006.01)
*A61B 17/34* (2006.01)

(52) U.S. Cl.
CPC ....... *A61M 25/0082* (2013.01); *A61N 1/0573* (2013.01); *A61N 1/37205* (2013.01); *A61N 1/37512* (2017.08); *A61N 2001/058* (2013.01)

(58) Field of Classification Search
USPC .......................................................... 607/9
See application file for complete search history.

(56) References Cited

U.S. PATENT DOCUMENTS

| | | | |
|---|---|---|---|
| 5,908,381 A | 6/1999 | Aznoian et al. | |
| 6,181,973 B1 | 1/2001 | Ceron et al. | |
| 6,224,725 B1 | 5/2001 | Glocker | |
| 6,395,017 B1 | 5/2002 | Dwyer et al. | |
| 6,409,674 B1 | 6/2002 | Brockway et al. | |
| 6,497,803 B2 | 12/2002 | Glocker et al. | |
| 6,551,477 B2 | 4/2003 | Glocker et al. | |
| 6,582,441 B1 | 6/2003 | He et al. | |
| 6,638,268 B2 | 10/2003 | Niazi | |
| 6,786,918 B1 | 9/2004 | Krivoruchko et al. | |
| 7,248,913 B2 | 7/2007 | Hassett | |
| 7,321,798 B2 | 1/2008 | Muhlenberg et al. | |
| 7,381,216 B2 | 6/2008 | Buzzard et al. | |
| 7,499,758 B2 | 3/2009 | Cates et al. | |
| 7,509,169 B2 | 3/2009 | Eigler et al. | |
| 7,608,099 B2 | 10/2009 | Johnson et al. | |
| 7,666,203 B2 | 2/2010 | Chanduszko et al. | |
| 7,678,081 B2 | 3/2010 | Whiting et al. | |
| 7,799,037 B1 | 9/2010 | He et al. | |
| 7,840,281 B2 | 11/2010 | Kveen et al. | |
| 7,937,161 B2 | 5/2011 | Hastings et al. | |
| 3,002,822 A1 | 8/2011 | Glocker et al. | |
| 7,993,351 B2 | 8/2011 | Worley et al. | |
| 8,010,209 B2 | 8/2011 | Jacobson | |
| 8,103,361 B2 | 1/2012 | Moser | |
| 8,185,213 B2 | 5/2012 | Kveen et al. | |
| 8,267,987 B2 | 9/2012 | Johnson et al. | |
| 8,352,028 B2 | 1/2013 | Wenger | |
| 8,364,280 B2 | 1/2013 | Marnfeldt et al. | |
| 8,382,813 B2 | 2/2013 | Shumer | |
| 8,428,750 B2 | 4/2013 | Kolberg | |
| 8,478,431 B2 | 7/2013 | Griswold et al. | |
| 8,504,156 B2 | 8/2013 | Bonner et al. | |
| 8,527,068 B2 | 9/2013 | Ostroff | |
| 8,532,790 B2 | 9/2013 | Griswold | |
| 8,548,605 B2 | 10/2013 | Ollivier | |
| 8,615,310 B2 | 12/2013 | Khairkhahan et al. | |
| 8,634,912 B2 | 1/2014 | Bornzin et al. | |
| 8,721,587 B2 | 5/2014 | Berthiaume et al. | |
| 8,727,996 B2 | 5/2014 | Allan et al. | |
| 8,758,365 B2 | 6/2014 | Bonner et al. | |
| 8,855,789 B2 | 10/2014 | Jacobson | |
| 8,894,824 B2 | 11/2014 | Glocker et al. | |
| 8,903,513 B2 | 12/2014 | Ollivier | |
| 8,926,588 B2 | 1/2015 | Berthiaume et al. | |
| 8,945,145 B2 | 2/2015 | Tran et al. | |
| 8,945,146 B2 | 2/2015 | Steingisser et al. | |
| 8,948,883 B2 | 2/2015 | Eggen et al. | |
| 8,958,892 B2 | 2/2015 | Khairkhahan et al. | |
| 9,020,611 B2 | 4/2015 | Khairkhahan et al. | |
| 9,072,872 B2 | 7/2015 | Asleson et al. | |
| 9,101,281 B2 | 8/2015 | Reinert et al. | |
| 9,119,959 B2 | 9/2015 | Rys et al. | |
| 9,126,032 B2 | 9/2015 | Khairkhahan et al. | |
| 9,155,882 B2 | 10/2015 | Grubac et al. | |
| 9,168,372 B2 | 10/2015 | Fain | |
| 9,204,842 B2 | 12/2015 | Mothilal et al. | |
| 9,205,225 B2 | 12/2015 | Khairkhahan et al. | |
| 9,216,293 B2 | 12/2015 | Berthiaume et al. | |
| 9,220,906 B2 | 12/2015 | Griswold et al. | |
| 9,238,145 B2 | 1/2016 | Wenzel et al. | |
| 9,242,102 B2 | 1/2016 | Khairkhahan et al. | |
| 9,272,155 B2 | 3/2016 | Ostroff | |
| 9,283,381 B2 | 3/2016 | Grubac et al. | |
| 9,283,382 B2 | 3/2016 | Berthiaume et al. | |
| 9,283,392 B2 | 3/2016 | Moore et al. | |
| 9,308,365 B2 | 4/2016 | Nordstrom et al. | |
| 9,308,374 B2 | 4/2016 | Kveen et al. | |
| 9,339,197 B2 | 5/2016 | Griswold et al. | |
| 9,351,648 B2 | 5/2016 | Mothilal et al. | |
| 9,358,387 B2 | 6/2016 | Suwito et al. | |
| 9,414,857 B2 | 8/2016 | Wood et al. | |
| 9,421,384 B2 | 8/2016 | Taff et al. | |
| 9,433,780 B2 | 9/2016 | Regnier et al. | |
| 9,446,248 B2 | 9/2016 | Sheldon et al. | |
| 9,463,315 B2 | 10/2016 | Bornzin et al. | |
| 9,468,773 B1 | 10/2016 | Anderson et al. | |
| 9,504,820 B2 | 11/2016 | Bonner et al. | |
| 9,511,236 B2 | 12/2016 | Varady et al. | |
| 9,517,336 B2 | 12/2016 | Eggen et al. | |
| 9,517,337 B2 | 12/2016 | Ollivier | |
| 9,526,522 B2 | 12/2016 | Wood et al. | |
| 9,526,891 B2 | 12/2016 | Eggen et al. | |
| 9,539,423 B2 | 1/2017 | Bonner et al. | |
| 9,555,236 B2 | 1/2017 | Regnier et al. | |
| 9,579,500 B2 | 2/2017 | Rys et al. | |
| 9,610,454 B2 | 4/2017 | Doan et al. | |
| 9,623,234 B2 | 4/2017 | Anderson | |
| 9,662,487 B2 | 5/2017 | Kveen et al. | |
| 9,675,798 B2 | 6/2017 | Grubac et al. | |
| 9,717,421 B2 | 8/2017 | Griswold et al. | |
| 9,724,507 B2 | 8/2017 | Wood et al. | |
| 9,750,931 B2 | 9/2017 | Wood et al. | |
| 9,764,139 B2 | 9/2017 | Christensen | |
| 9,775,982 B2 | 10/2017 | Grubac et al. | |
| 9,808,617 B2 | 11/2017 | Ostroff et al. | |
| 9,808,629 B2 | 11/2017 | Steingisser et al. | |
| 9,814,896 B2 | 11/2017 | Solem | |
| 9,833,625 B2 | 12/2017 | Waldhauser et al. | |
| 9,833,626 B2 | 12/2017 | Klimovitch et al. | |
| 9,844,659 B2 | 12/2017 | Grubac et al. | |
| 9,844,664 B2 | 12/2017 | McEvoy et al. | |
| 9,861,815 B2 | 1/2018 | Tran et al. | |
| 9,867,982 B2 | 1/2018 | Berthiaume et al. | |
| 2003/0078618 A1 | 4/2003 | Fey et al. | |
| 2005/0101984 A1 | 5/2005 | Chanduszko et al. | |
| 2005/0165472 A1 | 7/2005 | Glocker | |
| 2005/0209653 A1 | 9/2005 | Herbert et al. | |
| 2005/0267555 A1 | 12/2005 | Marnfeldt et al. | |
| 2006/0009737 A1 | 1/2006 | Whiting et al. | |
| 2009/0082828 A1 | 3/2009 | Ostroff | |
| 2010/0274227 A1 | 10/2010 | Khairkhahan et al. | |
| 2011/0112548 A1 | 5/2011 | Fifer et al. | |
| 2011/0270339 A1 | 11/2011 | Murray, III et al. | |
| 2011/0270340 A1 | 11/2011 | Pellegrini et al. | |
| 2012/0095539 A1 | 4/2012 | Khairkhahan et al. | |
| 2012/0109148 A1 | 5/2012 | Bonner et al. | |
| 2012/0165827 A1* | 6/2012 | Khairkhahan | A61N 1/3756 606/129 |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2013/0012925 A1 | 1/2013 | Berthiaume et al. | |
| 2013/0035636 A1 | 2/2013 | Beasley et al. | |
| 2013/0103047 A1 | 4/2013 | Steingisser et al. | |
| 2013/0253342 A1 | 9/2013 | Griswold et al. | |
| 2013/0253346 A1 | 9/2013 | Griswold et al. | |
| 2014/0018818 A1 | 1/2014 | Somogyi et al. | |
| 2014/0324145 A1 | 10/2014 | Eggen et al. | |
| 2014/0378991 A1 | 12/2014 | Ollivier | |
| 2015/0039070 A1 | 2/2015 | Kuhn et al. | |
| 2015/0045868 A1 | 2/2015 | Bonner et al. | |
| 2015/0051609 A1 | 2/2015 | Schmidt et al. | |

(56) References Cited

U.S. PATENT DOCUMENTS

| | | |
|---|---|---|
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1* | 2/2015 | Schmidt ............... A61N 1/3756 606/129 |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1 | 4/2016 | Eidenschink et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | | |
|---|---|---|---|
| EP | 2651502 B1 | 11/2016 | |
| EP | 2771064 B1 | 1/2017 | |
| EP | 2780077 B1 | 1/2017 | |
| WO | 2016065058 A1 | 4/2016 | |
| WO | WO-2016065058 A1 * | 4/2016 | ........... A61N 1/0587 |
| WO | 2016172106 A1 | 10/2016 | |

* cited by examiner

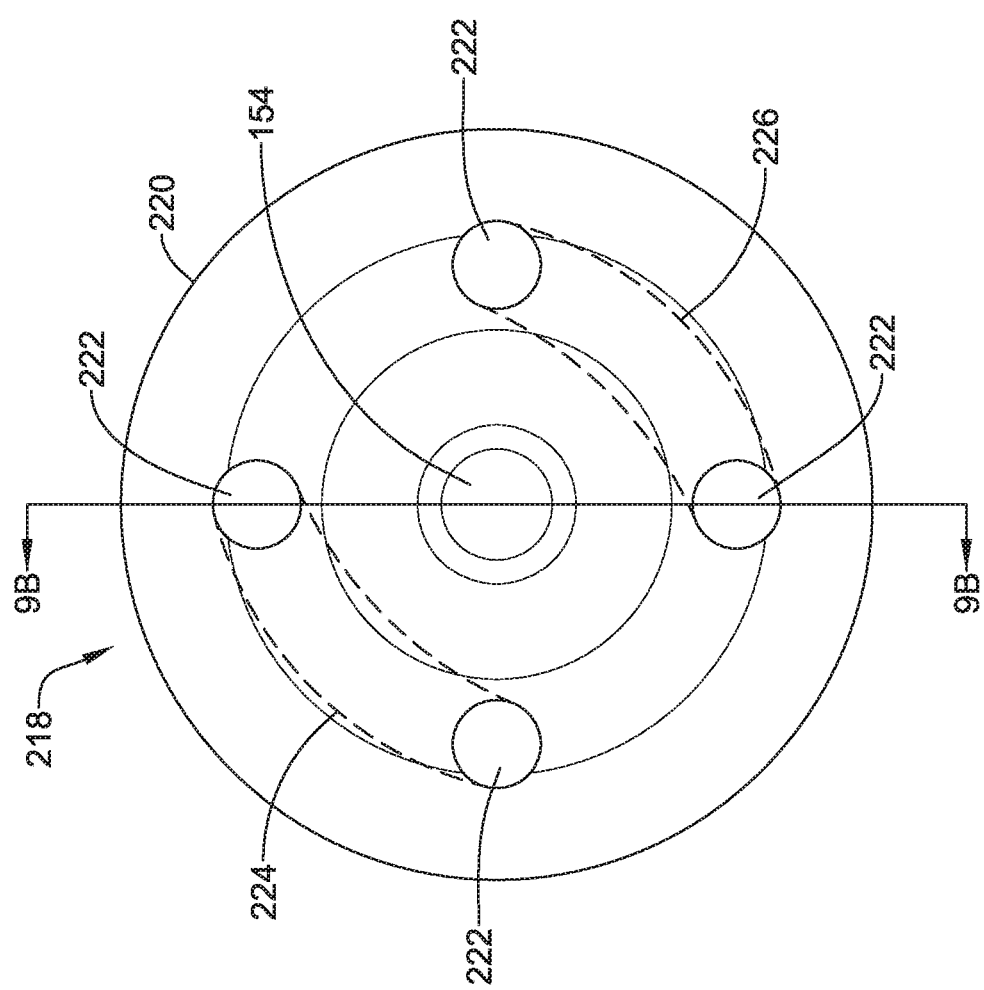

DELIVERY DEVICES AND METHODS FOR LEADLESS CARDIAC DEVICES

CROSS REFERENCE TO RELATED APPLICATIONS

This application is a continuation of U.S. application Ser. No. 15/879,937, filed Jan. 25, 2018, now issued as U.S. Pat. No. 10,773,089, which claims the benefit of and priority to U.S. Provisional Patent Application Ser. No. 62/450,727, filed Jan. 26, 2017, the entire disclosures of which are incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices. In an example of the disclosure, a delivery device for delivering an implantable leadless pacing device includes an outer tubular member having an outer tubular member lumen extending from a proximal end to a distal end thereof and an intermediate tubular member that is coaxially and slidingly disposed within the outer tubular member lumen and itself includes an intermediate tubular member lumen extending from a proximal end to a distal end thereof. An inner tubular member is coaxially and slidingly disposed within the intermediate tubular member lumen and itself includes an inner tubular member lumen extending from a proximal end to a distal end thereof. A distal holding section extends distally of a distal end of the intermediate tubular member and defines a cavity therein for receiving an implantable leadless pacing device. A deployment funnel is secured relative to the distal end of the inner tubular member and is moveable between an advanced position in which the deployment funnel extends distally within the distal holding section and a retracted position in which the deployment funnel is seated within a proximal portion of the distal holding section. The deployment funnel is configured to permit fluid flow from the distal end of the intermediate tubular member lumen into the distal holding section when the deployment funnel is in the retracted position.

Alternatively or additionally to any embodiment above, the deployment funnel may include one or more apertures extending through the deployment funnel that are in fluid communication with the intermediate tubular member lumen so that fluid can flow from the distal end of the intermediate tubular member lumen and pass through the one or more apertures into the distal holding section.

Alternatively or additionally to any embodiment above, the deployment funnel may include one or more grooves that are in fluid communication with the intermediate tubular member lumen so that fluid can flow from the distal end of the intermediate tubular member lumen and pass through the one or more grooves into the distal holding section.

Alternatively or additionally to any embodiment above, at least a portion of the deployment funnel may include a porous material that enables fluid flow through pores thereof.

Alternatively or additionally to any embodiment above, at least a portion of the deployment funnel may include a scaffolding material including voids that enable fluid flow therethrough.

Alternatively or additionally to any embodiment above, the deployment funnel may be further configured to provide a fluid coupling between the inner tubular member lumen and the distal holding section when the deployment funnel is in the retracted position.

Alternatively or additionally to any embodiment above, the deployment funnel may include a central aperture that aligns with the inner tubular member lumen.

Alternatively or additionally to any embodiment above, the inner tubular member lumen may extend proximally to a fluid port.

Alternatively or additionally to any embodiment above, the intermediate tubular member lumen may extend proximally to a fluid port.

In another example of the disclosure, a delivery device for delivering an implantable leadless pacing device includes an outer tubular member defining an outer tubular member lumen extending from a proximal end to a distal end thereof and an intermediate tubular member that is moveably disposed within the outer tubular member lumen and itself defines an intermediate tubular member lumen extending from a proximal end to a distal end thereof. A distal holding section extends distally of a distal end of the intermediate tubular member and is configured to accommodate an implantable leadless pacing device at least partially within the distal holding section. The intermediate tubular member is moveable between a retracted position in which a proximal portion of the distal holding section seats within the outer tubular member lumen and an extended position in which the proximal portion of the distal holding section extends distally from the outer tubular member lumen. An inner tubular member is moveably disposed within the intermediate tubular member lumen and itself defines an inner tubular member lumen extending from a proximal end to a distal end thereof. A deployment funnel is secured relative to the distal end of the inner tubular member and the inner tubular member is moveable between an extended position in which the deployment funnel extends distally within the distal holding section and a retracted position in which the deployment funnel is seated within a proximal portion of the distal holding section. The deployment funnel is configured to permit fluid flow from the distal end of the intermediate tubular member lumen into the distal holding section when in the retracted position.

Alternatively or additionally to any embodiment above, the deployment funnel may include one or more apertures extending through the deployment funnel in order to permit fluid to flow past the deployment funnel in the retracted position.

Alternatively or additionally to any embodiment above, the deployment funnel may include one or more grooves on a surface of the deployment funnel in order to permit fluid to flow past the deployment funnel in the retracted position.

Alternatively or additionally to any embodiment above, at least a portion of the deployment funnel may include a porous material that enables fluid flow therethrough.

Alternatively or additionally to any embodiment above, the outer tubular member lumen may extend proximally to a fluid port such that the outer tubular member lumen may be flushed with fluid with the intermediate tubular member in its extended position.

Alternatively or additionally to any embodiment above, the intermediate tubular member lumen may extend proximally to a fluid port such that the intermediate tubular member lumen may be flushed with fluid regardless of a position of the inner tubular member relative to the intermediate tubular member.

Alternatively or additionally to any embodiment above, the inner tubular member includes an aperture proximate the distal end thereof providing a fluid pathway between the intermediate tubular member lumen and the inner tubular member lumen permitting fluid to pass from the intermediate tubular member lumen into the inner tubular member lumen and distally through the deployment funnel into the distal holding section.

Alternatively or additionally to any embodiment above, the intermediate tubular member includes an aperture proximate the distal end thereof providing a fluid pathway between the outer tubular member lumen and the intermediate tubular member lumen permitting fluid to pass from the outer tubular member lumen into the intermediate tubular member lumen and distally into the distal holding section.

In another example of the disclosure, a delivery system for delivering a leadless cardiac pacemaker (LCP) includes a deflection shaft defining a deflection shaft lumen and an extension shaft extending through the deflection shaft lumen, the extension shaft defining an extension shaft lumen. An LCP sleeve is secured to a distal end of the extension shaft and extends distally therefrom, the LCP sleeve configured to accommodate an LCP at least partially within the LCP sleeve for delivery. A deployment shaft extends through the extension shaft lumen and itself defines a deployment shaft lumen. A deployment funnel is secured to a distal end of the deployment shaft and is configured to engage the LCP for holding the LCP in place while the LCP sleeve is withdrawn proximally relative to the LCP. The deployment funnel is configured to accommodate a tether extending within the deployment shaft lumen and through a central aperture of the deployment funnel that aligns with the deployment shaft lumen, the deployment funnel including one or more fluid structures that enable fluid to flow from the extension shaft lumen and distally beyond the deployment funnel into the LCP sleeve.

Alternatively or additionally to any embodiment above, the delivery system may further include a handle assembly configured to control a position of the deployment shaft relative to the extension shaft and/or a position of the extension shaft relative to the deflection shaft.

Alternatively or additionally to any embodiment above, the handle assembly may include a first fluid port fluidly coupled with the deflection shaft lumen.

Alternatively or additionally to any embodiment above, the handle assembly may include a second fluid port fluidly coupled with the extension shaft lumen.

Alternatively or additionally to any embodiment above, the handle assembly may include a third fluid port fluidly coupled with the deployment shaft lumen.

Alternatively or additionally to any embodiment above, the deployment funnel comprises one or more grooves on a surface of the deployment funnel in order to permit fluid to flow past the deployment funnel into the LCP sleeve.

Alternatively or additionally to any embodiment above, the one or more grooves are formed on a radially outward facing surface of the deployment funnel seated against a hub portion of the LCP sleeve.

Alternatively or additionally to any embodiment above, the one or more grooves are formed on a radially inward facing surface of the deployment funnel seated against a head portion of a docking member of the LCP.

Alternatively or additionally to any embodiment above, the deployment shaft includes an aperture extending through a sidewall thereof providing a fluid pathway between the extension shaft lumen and the deployment shaft lumen permitting fluid to pass from the extension shaft lumen into the deployment shaft lumen and distally through the deployment funnel into the LCP sleeve.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 9A is an end view of a deployment funnel that can be used as a portion of the delivery device of FIG. 3;

Figure 1:
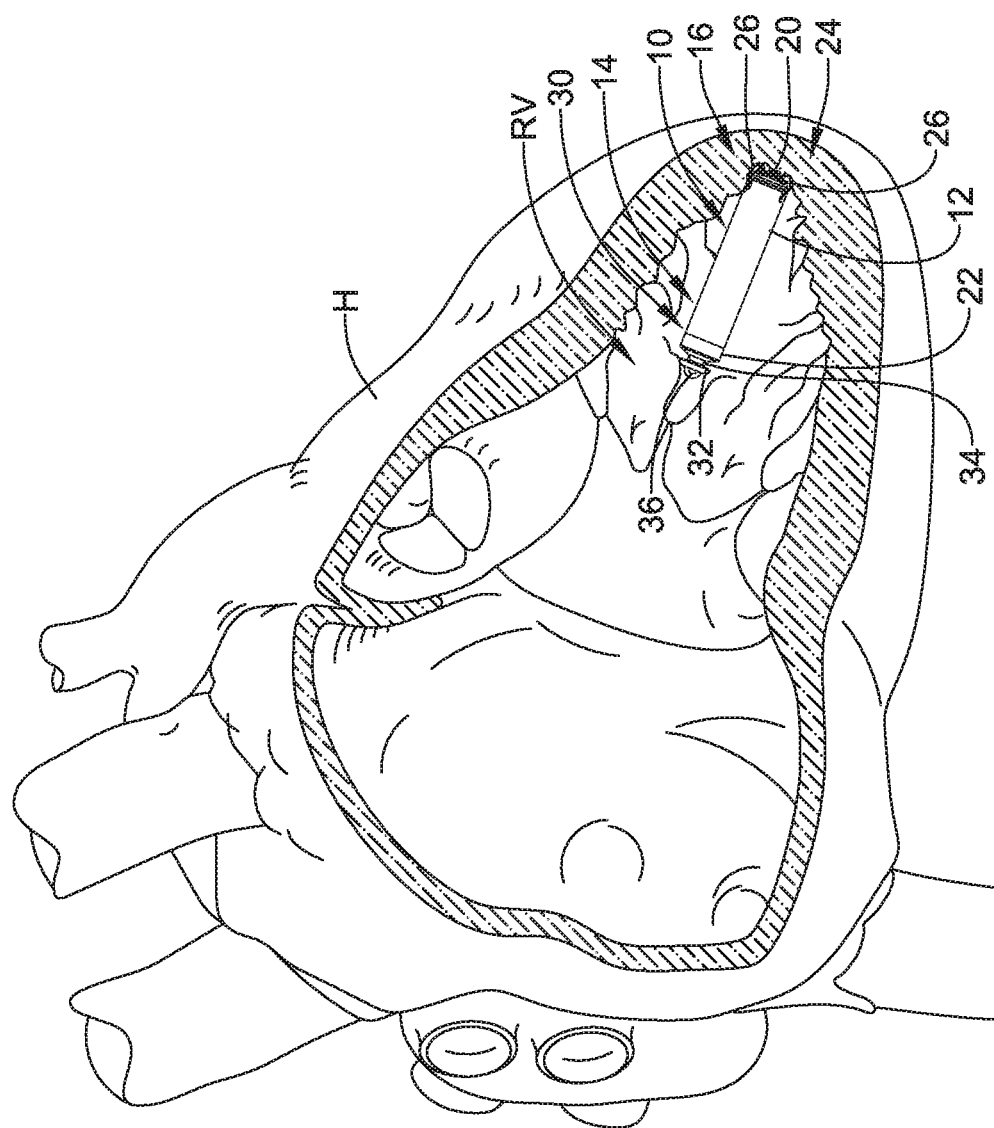
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
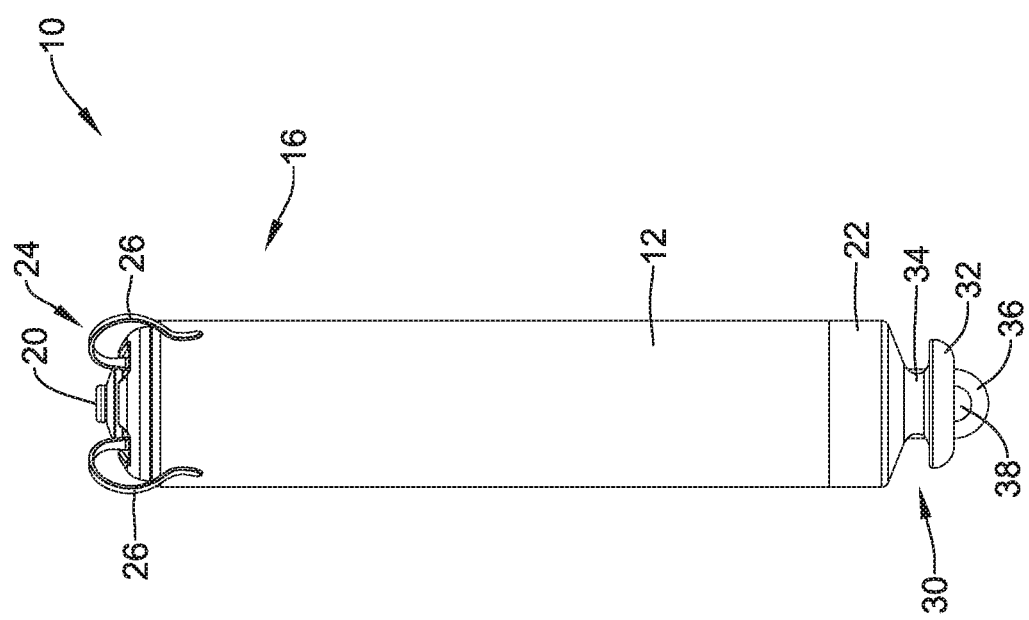
FIG. 2 is a side view of an example implantable leadless cardiac pacing device.

FIG. 1 illustrates an example implantable leadless cardiac pacing device 10 (e.g., a leadless pacemaker) implanted in a chamber of a heart H, such as the right ventricle RV. In some cases, the implantable device 10 may be referred to as being a leadless cardiac pacemaker (LCP). A side view of the illustrative implantable device 10 is shown in FIG. 2. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks or tines 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 3:
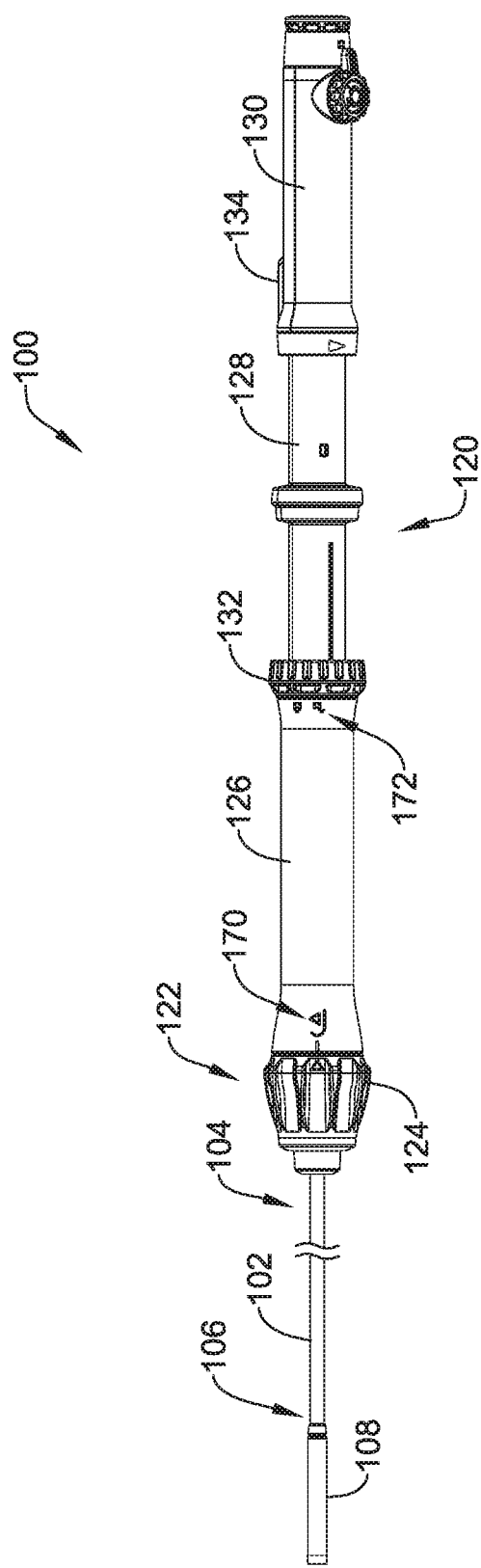
FIG. 3 is a plan view of an example delivery device for an implantable leadless cardiac pacing device.

FIG. 3 is a plan view of an illustrative delivery device 100, such as a catheter, that may be used to deliver the implantable device 10. The delivery device 100 may include an outer tubular member 102 having a proximal section 104 and a distal section 106. In some cases, the outer tubular member 102 may be considered as being a deflection shaft. An intermediate tubular member 110 may be longitudinally slidably disposed within an outer tubular member lumen 150 (or a deflection shaft lumen) of the outer tubular member 102 (see e.g. FIG. 4). The intermediate tubular member 110 may be considered as being an extension shaft. An inner tubular member 116 may be longitudinally slidably disposed within an intermediate tubular member lumen 152 (or extension shaft lumen) of the intermediate tubular member 110 (see e.g. FIG. 4). A distal holding section 108 may be attached to a distal end portion 114 of the intermediate tubular member 110. In some cases, the distal holding section 108 may be considered as being an LCP sleeve, particularly if configured to accommodate a leadless cardiac pacemaker (LCP) as the implantable device 10. The delivery device 100 may also include a handle assembly 120 positioned adjacent to the proximal section 104 of the outer tubular member 102. In some embodiments, the outer tubular member 102 may include at least a section thereof that has an outer diameter D2 that is less than the outer diameter D1 of at least a portion of the holding section 108 (see e.g. FIG. 4).

Figure 4:
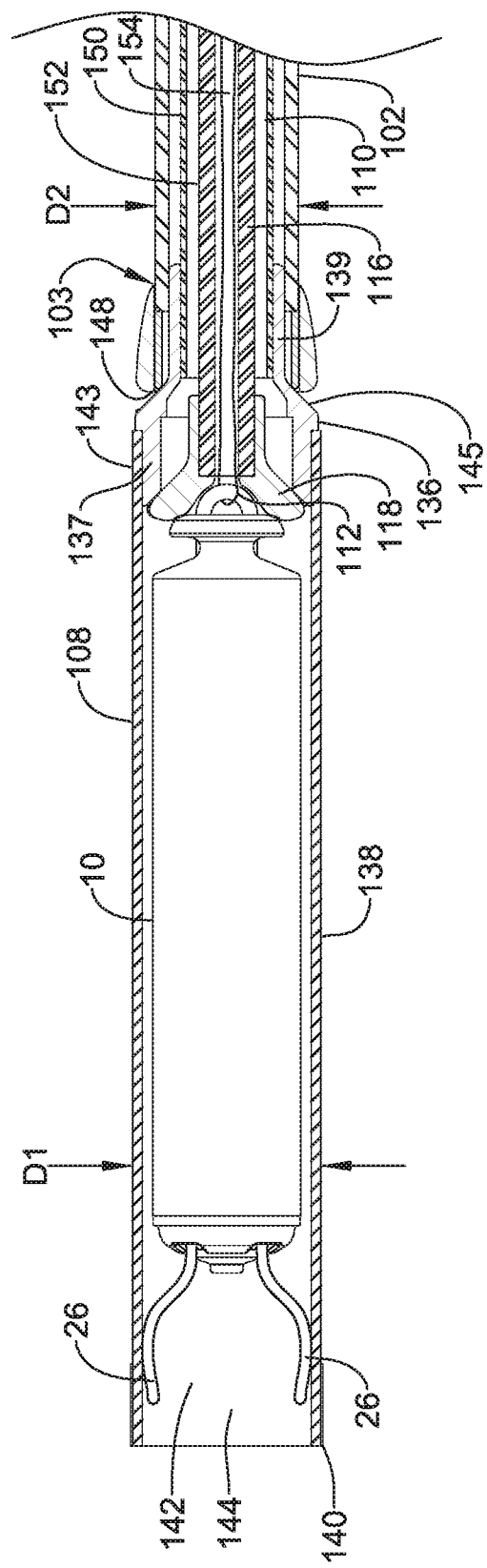
FIG. 4 is a partial cross-sectional side view of the distal portion of the delivery device of FIG. 3.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g. FIG. 4). In some cases, the inner tubular member 116 may be considered as being a deployment shaft. The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The distal holding section 108 may be configured to receive the implantable device 10 therein. For example, referring to FIG. 4, which illustrates a cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 140 of the delivery device 100 will likely come into contact with tissue adjacent the target site (e.g. cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some embodiments, all or a portion of the distal holding section 108 may include an inner surface that may be configured to resist getting caught on the fixation mechanism 24, such as the one or more, or a plurality of hooks or tines 26 on the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within the intermediate tubular member lumen 152 of the intermediate tubular member 110. The inner tubular member 116 may be engaged by a user near or at the third hub portion 130, and extend through the intermediate tubular member lumen 152 of the intermediate tubular member 110 and into the distal holding section 108. In some cases, the inner tubular member 116 may include a deployment funnel 118 that may, for example, be capable of engaging the device 10, and the inner tubular member 116 may be used to "push" the device 10 out from the distal holding section 108 so as to deploy and anchor device 10 within a target region (e.g., a region of the heart such as the right ventricle). The inner tubular member 116 may have an inner tubular member lumen 154 extending from the proximal end 117 to and/or through the deployment funnel 118. A tether 112 or other retaining feature may be used to releasably secure the device 10 to the delivery device 100. In some instances, the tether 112 may be a single or unitary length of material that may extend from a proximal end 117 of the inner tubular member lumen 154, out through the deployment funnel 118, through the opening 38 of the device 10 and return to the proximal end 117 of the inner tubular member 116 through the inner tubular member lumen 154 such that both ends of the tether 112 are positioned adjacent to the third hub portion 130. In some instances, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 3, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 4, the distal holding section 108 may be affixed to a distal end portion 114 of the intermediate tubular member 110. The distal holding section 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 5:
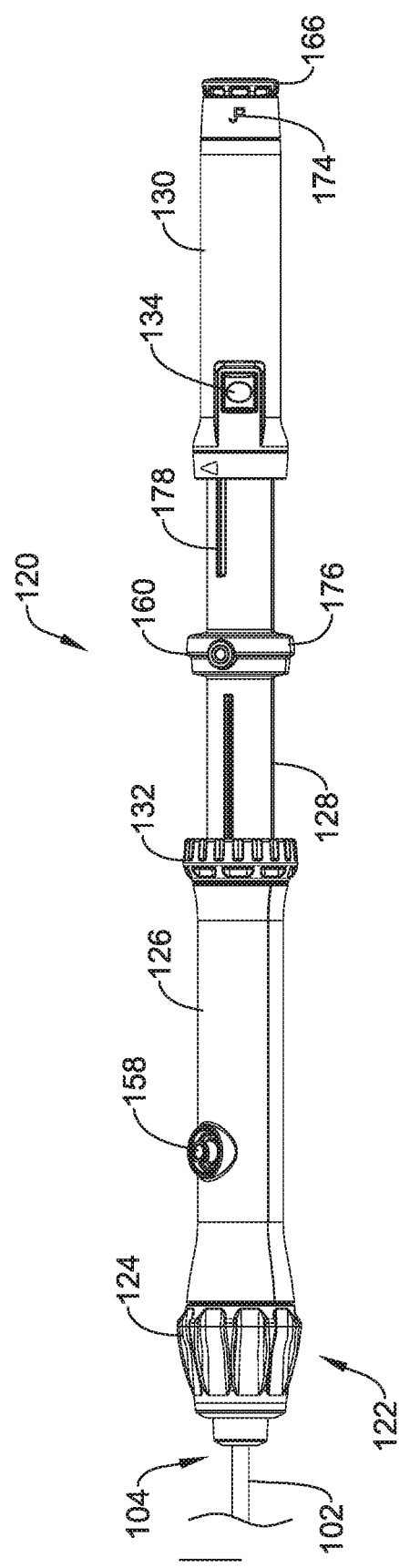
FIG. 5 is a top view of the handle of the illustrative delivery device of FIG. 3.
Figure 6:
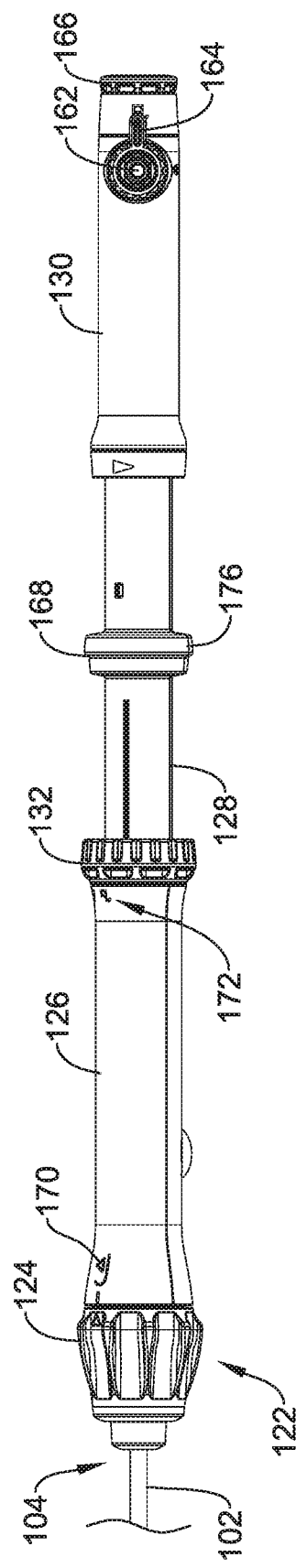
FIG. 6 is a bottom view of the handle of the illustrative delivery device of FIG. 3.

FIG. 5 illustrates a top view of the handle assembly 120 of the delivery device 100 and FIG. 6 illustrates a bottom view of the handle assembly, approximately 180° from the view shown in FIG. 5. The handle assembly 120 may include one or more ports 158, 160, 162 for delivering fluids, such as, but not limited to, a contrast and/or flushing fluid to the cavity 142 of the distal holding section 108. The flush ports 158, 160, 162 may be in fluid communication with the lumens 150, 152, 154 of the outer, intermediate or inner tubular members 102,110, 116, as desired. In some cases, and as an illustrative but non-limiting example, the flush port 158 may be in fluid communication with the outer tubular member lumen 150 of the outer tubular member 102, the flush port 160 may be in fluid communication with the intermediate tubular member lumen 152 of the intermediate tubular member 110, and the flush port 162 may be in fluid communication with the inner tubular member lumen 154 of the inner tubular member 116.

In some cases, one or more of the flush ports 158, 160, 162 may be used to provide saline or another flushing to ensure that no air or debris remains within any of the lumens 150, 152, 154 prior to use of the delivery device 100. In some cases, one or more of the flush ports 158, 160, 162 may be used to provide a continuous supply of fluid such as but not limited to heparinized saline to one or more of the outer tubular member lumen 150, the intermediate tubular member lumen 152 and/or the inner tubular member 154 during delivery and deployment of the implantable device 10 to keep blood and debris from traveling proximally through one or more of the lumens 150, 152, 154 as well as to keep debris from clogging or otherwise interfering with operation of the delivery device 100.

Figure 7:
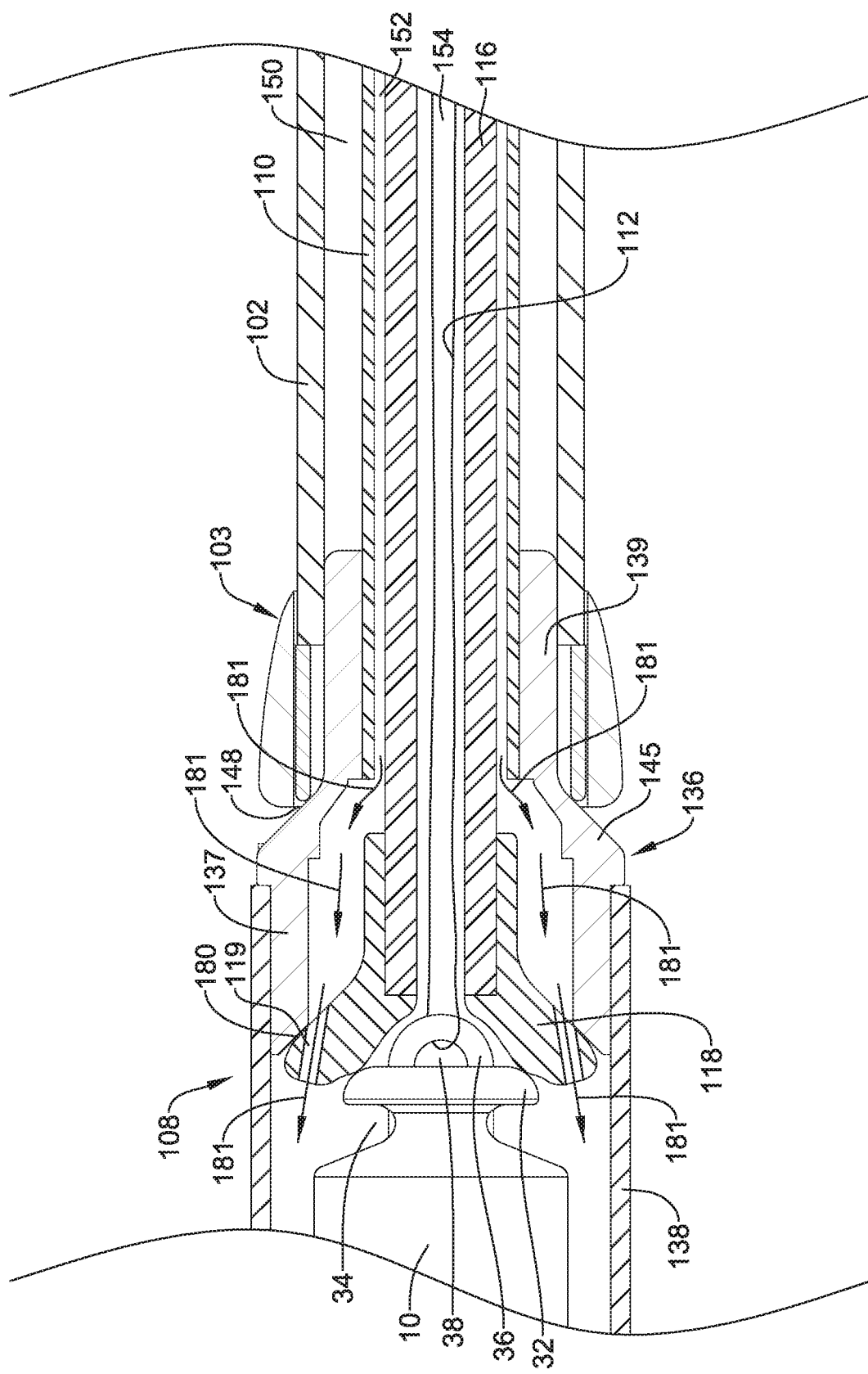
FIG. 7 is an enlarged partial cross-sectional view of a portion of the illustrative delivery device of FIG. 3, showing fluid paths through the delivery device.
Figure 8:
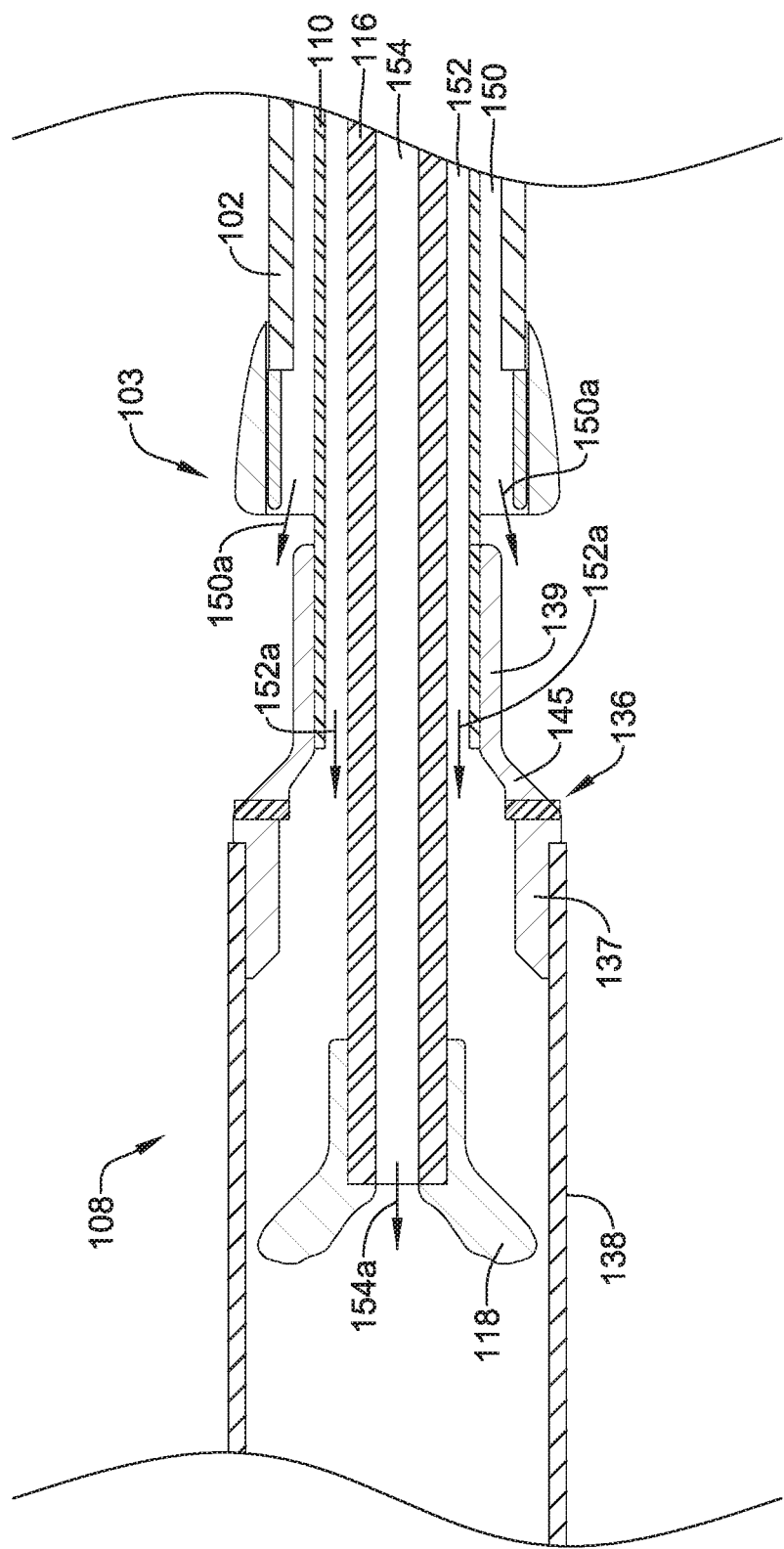
FIG. 8 is an enlarged partial cross-sectional view of a portion of the illustrative delivery device of FIG. 3, showing fluid paths through the delivery device.

FIGS. 7 and 8 illustrate fluid flow paths for each of the outer tubular member lumen 150, the intermediate tubular member lumen 152 and the inner tubular member 154 as well as demonstrating relative movement possible between the outer tubular member 102, the intermediate tubular member 110 and the inner tubular member 116 and how this relative movement can influence fluid flow paths.

FIG. 7 shows the outer tubular member 102, the intermediate tubular member 110 and the inner tubular member 116 in a configuration that may, for example, be used for deploying the implantable device 10. As noted with respect to FIG. 4, the tether 112 extends distally through the inner tubular member lumen 154 and the deployment funnel 118, and is coupled to the tether retention feature 36. For example, as shown in FIG. 7, the tether 112 passes through the opening 38 and thus around the tether retention structure 36 and extends proximally back through the inner tubular member lumen 154. It will be appreciated that the tether 112 does not interfere with fluid flow through the inner tubular member lumen 154. FIG. 8 shows the outer tubular member 102, the intermediate tubular member 110 and the inner tubular member 116 axially separated to show fluid flow paths. In comparing FIG. 7 and FIG. 8, it can be seen, for example, that the inner tubular member 116 may move axially relative to the intermediate tubular member 110, between an advanced position (FIG. 8) in which the deployment funnel 118 extends distally into or even through the distal holding section 108 and a retracted position (FIG. 7) in which the deployment funnel 118 seats into the hub portion 136 and contacts the hub portion 136 at a contact point 180 (FIG. 7). Similarly, the intermediate tubular member 110 may move between a retracted position (FIG. 7) in which a proximal portion of the distal holding section 108 (such as the hub portion 136) seats within the outer tubular member lumen 150 and an extended position (FIG. 8) in which the proximal portion of the distal holding section 108 (such as the hub portion 136) extends distally from the outer tubular member lumen 150.

With reference to FIG. 8, fluid paths for flushing the delivery device 100 during a medical procedure use are easily seen. For example, arrows 150a illustrate how fluid may flow through the outer tubular member lumen 150 and exterior of the distal holding section 108. Arrows 152a illustrate how fluid may flow through the intermediate tubular member lumen 152 and into/through the distal holding section 108. An arrow 154a illustrates how fluid may flow through the inner tubular member lumen 154 and into/through the distal holding section 108. In comparing FIG. 7 and FIG. 8, it will be appreciated that fluid may flow as indicated by the arrow 154a regardless of the position of the inner tubular member 116 (and hence the deployment funnel 118) relative to the intermediate tubular member 110. In some cases, there is a desire to be able to flush fluid through the intermediate tubular member lumen 152 and/or the outer tubular member lumen 150, even when the components are positioned as shown in FIG. 7. However, the hub portion 136 can be seen as potentially blocking fluid flow through the outer tubular member lumen 150 since the hub portion 136 may be abutting the distal end of the outer tubular member 102 in the retracted configuration of FIG. 7. In some cases, the hub portion 136 may include one or more fluid flow channels (grooves and/or apertures) that align with the outer tubular member lumen 150 and permit fluid flow therethrough.

Similarly, the deployment funnel 118, seated against the hub portion 136, can be seen as potentially blocking fluid flow through the intermediate tubular member lumen 152 into the distal holding section 108 but for fluid pathways formed between the interface between the deployment funnel 118 and the hub portion 136 of the distal holding section 108. In some cases, the deployment funnel 118 may include one or more fluid paths 119 that are formed through or along the deployment funnel 118. As indicated by arrows 181, fluid may flow through the intermediate tubular member lumen 152 and through the fluid paths 119 into the distal holding section 108. As a result, fluid may flow past the contact point 180 between the funnel 118 and the hub portion 136 that could otherwise block fluid flow. The fluid paths 119 may represent fluid channels such as one or more apertures extending through the deployment funnel 118 or grooves or recesses formed in an outer surface of the deployment funnel 118, for example.

FIGS. 9A through 14 provide illustrative but non-limiting examples of deployment funnels that include examples of the fluid paths and thus that may be configured to permit fluid flow from the intermediate tubular member lumen 152 and/or the inner tubular member lumen 154 to pass beyond the deployment funnel into the distal holding section 108 and thus enable fluid flushing both before and during use of the delivery device 100 while the deployment funnel is seated against the hub portion 136 of the distal holding section 108 and/or the head portion 32 of the docking member 30 is seated against the deployment funnel 118. While FIGS. 9A through 14 illustrate potential structural changes to the deployment funnel 118, and in some cases potential structural changes to one or more of the tubular members, it should be noted that in some cases, it is contemplated that rather than altering the deployment funnel 118, that the hub portion 136 itself may be altered to permit fluid flow. For example, grooves or channels could be formed within the distal end portion 137 of the hub portion 136 that would permit fluid flow past the deployment funnel 118.

Figure 9B:
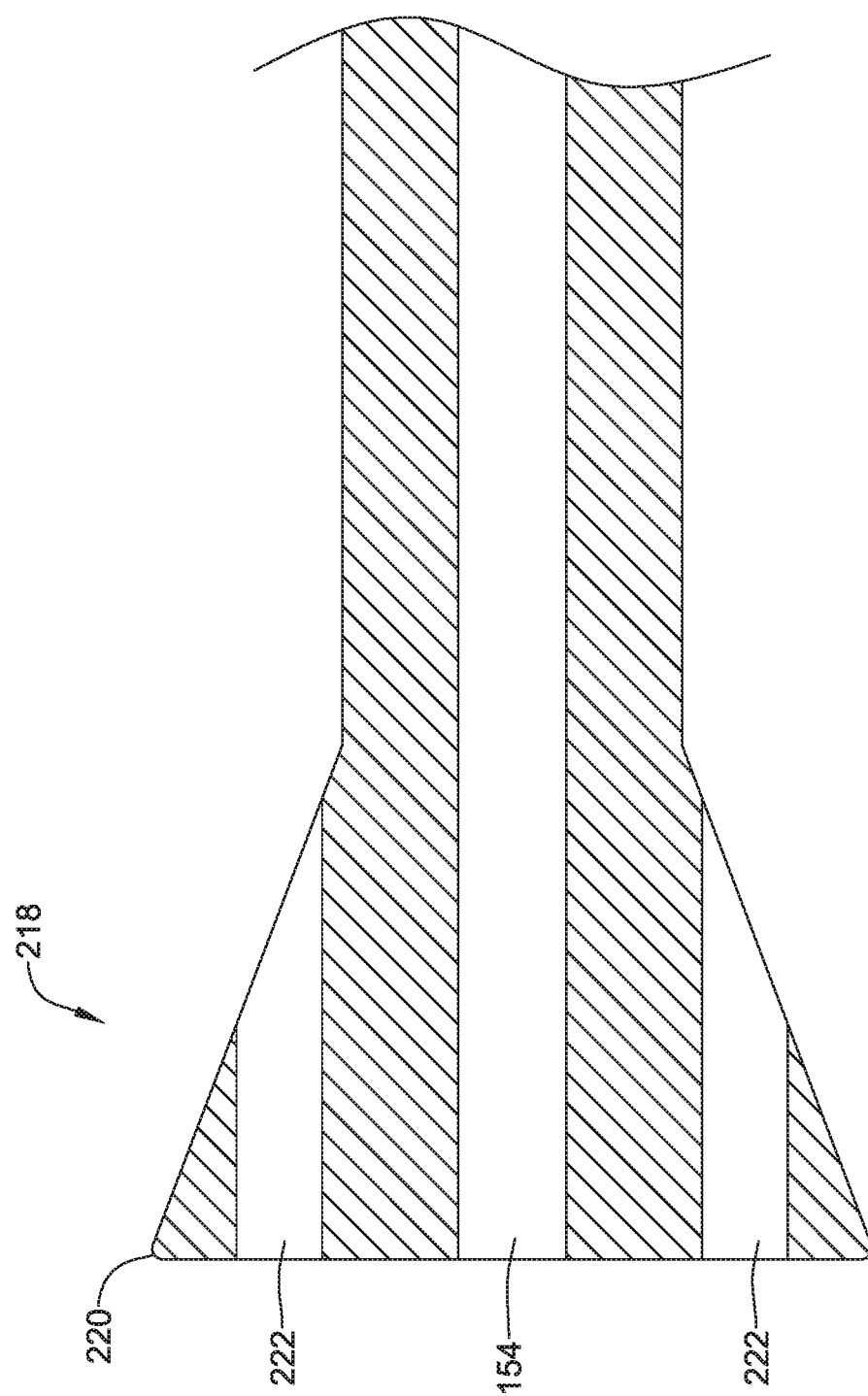
FIG. 9B is a cross-sectional view of the deployment funnel of FIG. 9A, taken along the 9B-9B line.

FIG. 9A is an end view of a deployment funnel 218 having an annular cross-sectional profile, at least about a periphery 220 of the deployment funnel 218 while FIG. 9B provides a corresponding cross-sectional view of the deployment funnel 218, taken along the line 9B-9B in FIG. 9A. The inner tubular member lumen 154 may be seen as extending centrally through the deployment funnel 218. In some cases, the deployment funnel 218 may include one or more flow channels, such as one or more, or a plurality of apertures 222 that extend through (e.g., axially through) the wall of the deployment funnel 218, thereby permitting fluid to flow through the apertures 222 and thus flow past the deployment funnel 218 and into the distal holding section 108 (FIG. 8). The apertures 222 may be mechanically formed through the deployment funnel 218, such as drilling the apertures 222 through the wall of the deployment funnel 218 from a proximally facing surface of the deployment funnel 218 to a distally facing surface of the deployment funnel 218. In some cases, the apertures 222 may instead be laser-cut.

While a total of four apertures 222 are shown, equidistantly spaced apart around the periphery 220, in some cases the deployment funnel 218 may include five, six or more distinct apertures 222. In some cases, the deployment funnel 218 may instead only have one, two, or three distinct apertures 222. While the apertures 222 are shown as being roughly circular, in some cases, one or more of the apertures 222 may take any desired shape. For example, one or more of the apertures 222 may be ovoid or polygonal. In some cases, one or more of the apertures 222 could be elongated in shape. For example, the deployment funnel 218 could include a first elongated slot 224 and a second elongated slot 226, each shown as extending between a pair of apertures 222. In some cases, the deployment funnel 218 could include additional elongated slots, as desired. These are just examples.

Figure 10:
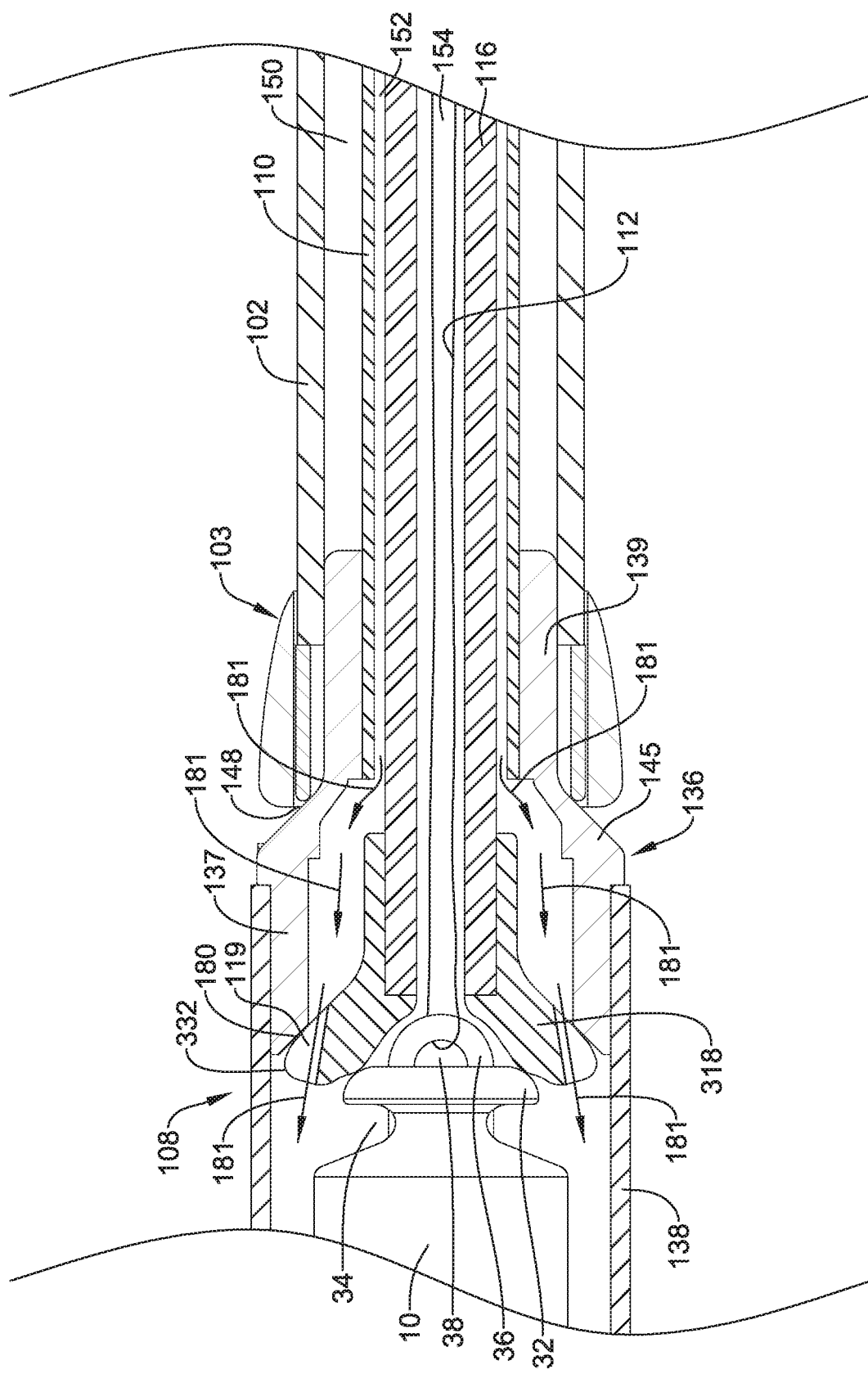
FIG. 10 is an enlarged partial cross-sectional view of a portion of an illustrative delivery device, showing fluid paths through the delivery device.

FIG. 10 shows the outer tubular member 102, the intermediate tubular member 110 and the inner tubular member 116 in a configuration that may, for example, be used for deploying the implantable device 10. As noted with respect to FIG. 4, the tether 112 extends distally through the inner tubular member lumen 154 and through the deployment funnel 318, and is coupled to the tether retention feature 36. For example, as shown in FIG. 10, the tether 112 passes through the opening 38 and thus around the tether retention structure 36 and extends proximally back through the inner tubular member lumen 154. It will be appreciated that the tether 112 does not interfere with fluid flow through the inner tubular member lumen 154.

Figure 11A:
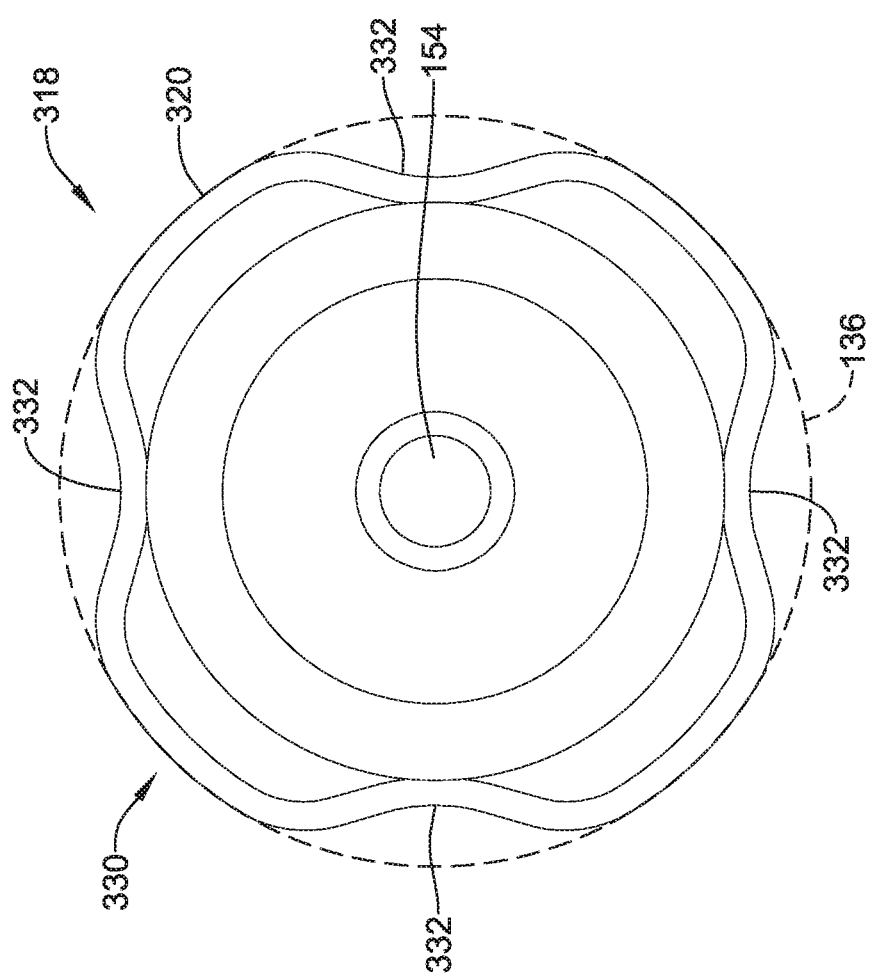
FIG. 11A is an end view of a deployment funnel that can be used as a portion of the delivery device of FIG. 10.
Figure 11B:
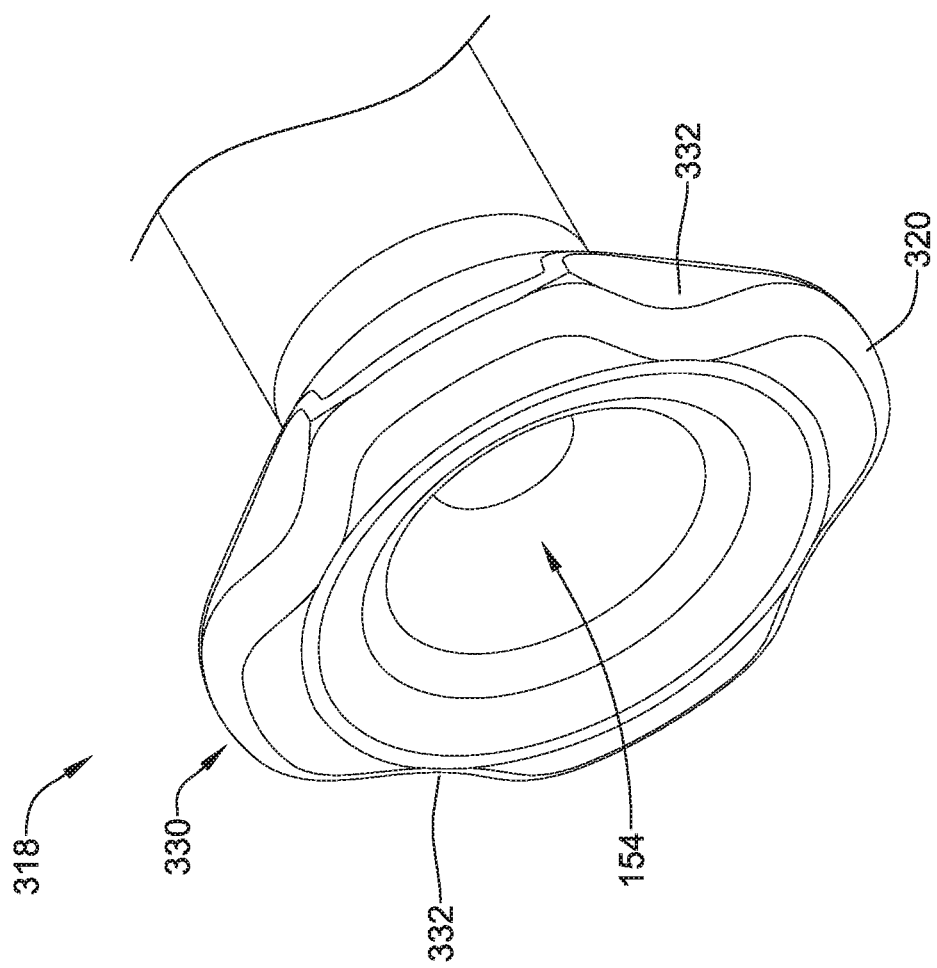
FIG. 11B is a perspective view of the deployment funnel of FIG. 11A.

In FIG. 10, a deployment funnel 318, as will be discussed with respect to FIG. 11A, is seen attached to the distal end of the inner tubular member 116 such that the inner tubular member lumen 154 extends through then central opening of the deployment funnel 318. Rather than including apertures 222 (FIGS. 9A and 9B) that permit fluid flow paths 119, the deployment funnel 318 includes one or more recesses or grooves 332 (FIG. 11A) formed in a radially outward facing surface 330 of the flared portion of the deployment funnel 318, providing a fluted periphery of the radially outward facing surface 330 of the deployment funnel 318. Turning to FIG. 11A, an end view of the deployment funnel 318 having a fluted periphery 320 is shown. FIG. 11B provides a perspective view of the deployment funnel 318. The inner tubular member lumen 154 may be seen as extending centrally through the deployment funnel 318. In some cases, the fluted periphery 320 includes one or more, or a plurality of recesses or grooves 332 that are molded or otherwise formed into an outer surface 330 of the deployment funnel 318. The outer surface 330 may be a proximally facing surface of the deployment funnel 318 with portions of the outer surface 330 contacting and/or seated against a surface of the hub portion 136 at contact points 180. For example, the protruding portions of the fluted periphery 320 positioned between the recesses or grooves 332 may be seated against the surface of the hub portion 136, while a fluid pathway may be defined between the surface of the hub portion 136 (shown as a dashed line to illustrate) and the surface of the funnel 318 defining the recesses or grooves 332. In some cases, the deployment funnel 318 may have a periphery with an annular profile, and the recesses or grooves 332 may instead be cut into the outer surface 330 of the deployment funnel 318. The recesses or grooves 332 may, for example, permit fluid flow past the deployment funnel 318 from the intermediate tubular member lumen 152 and thus into the distal holding section 108 (FIG. 8). The deployment funnel 318 may include one or more, or a plurality of recesses or grooves 332. While a total of four recesses or grooves 332 are shown, equidistantly spaced apart around the periphery 320, in some cases the deployment funnel 318 may include five, six or more distinct recesses or grooves 332. In some cases, the deployment funnel 218 may instead only have one, two, or three distinct recesses or grooves 332.

Figure 11C:
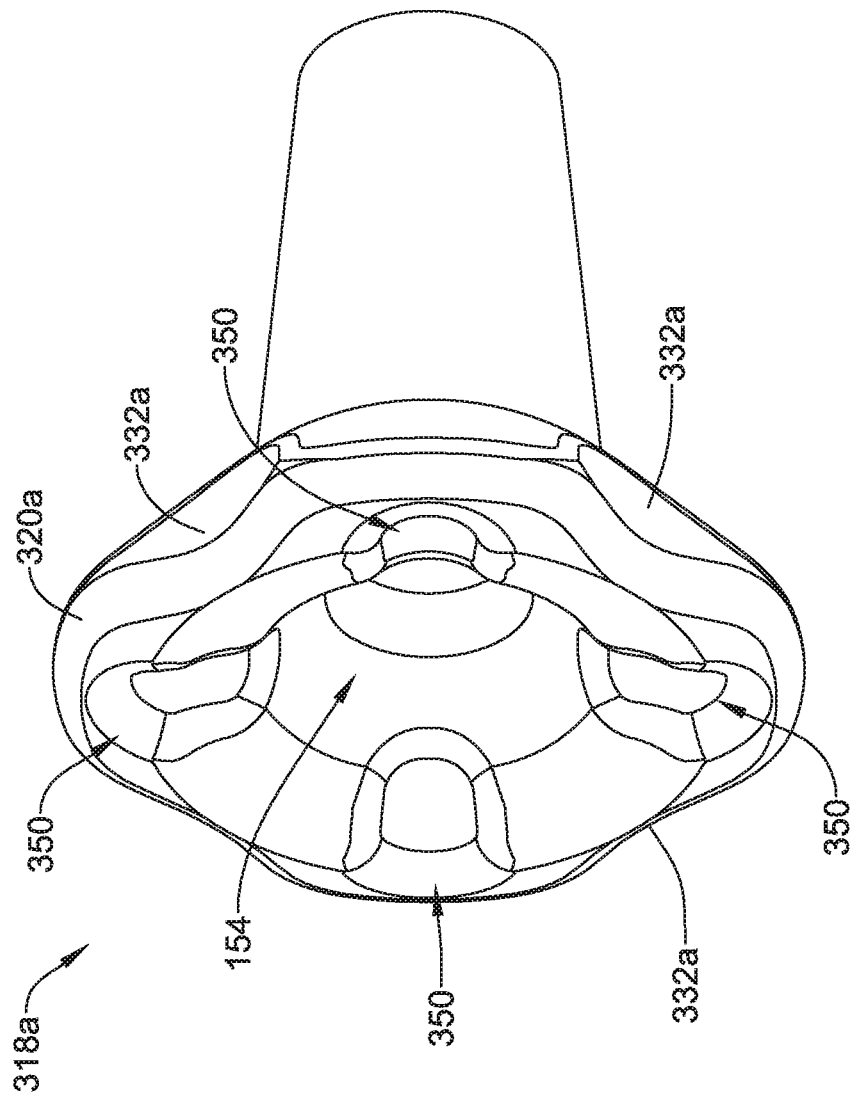
FIG. 11C is a perspective view of another deployment funnel that can be used as part of the delivery device of FIG. 10.
Figure 11D:
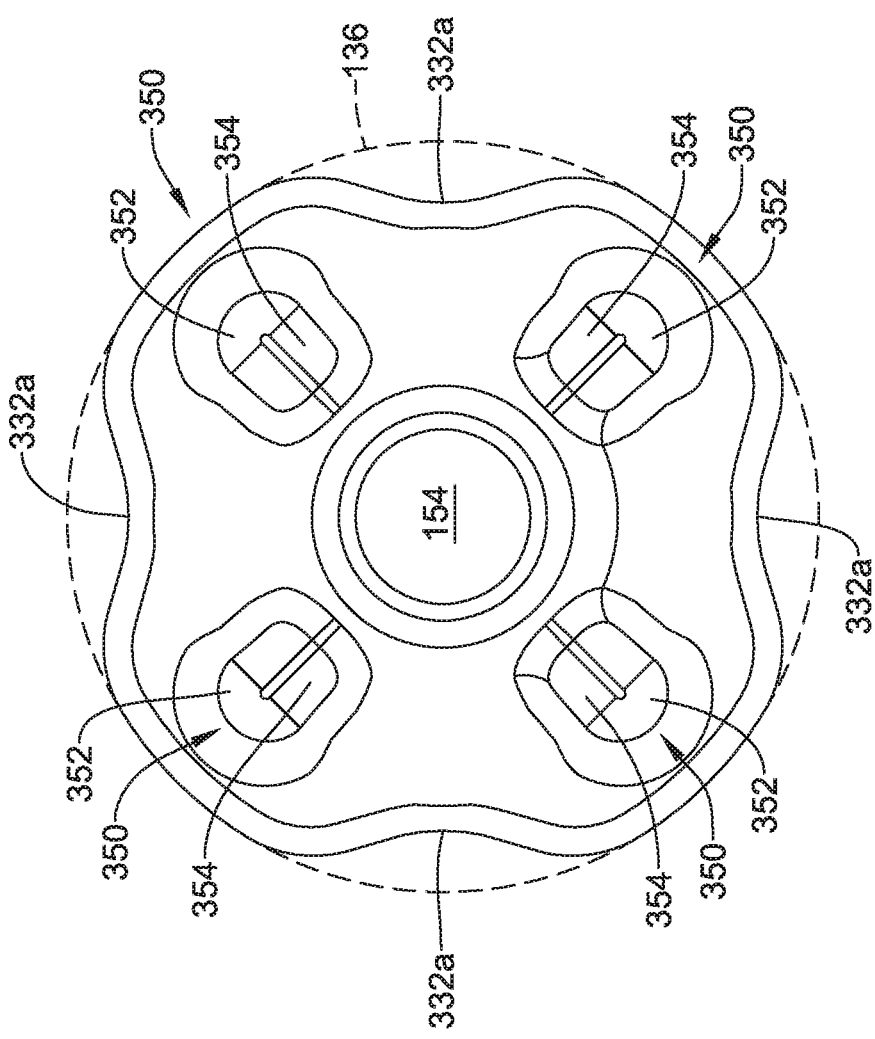
FIG. 11D is an end view of the deployment funnel of FIG. 11C.

FIG. 11C is a perspective view of a deployment funnel 318a that includes a fluted periphery 320a that includes one or more, or a plurality, of recesses or grooves 332a that are molded or otherwise formed into the deployment funnel 318a. FIG. 11D provides an end view of the deployment funnel 318a. In some cases, while portions of the deployment funnel 318a between the recesses or grooves 332a may contact or seat against a surface of the hub portion 136 at contact points 180, the recesses or grooves 332a may provide a fluid pathway defined between the surface of the hub portion 136 (shown as a dashed line to illustrate) and the surface of the funnel 318a defining the grooves 332a. In some cases, the deployment funnel 318a may have a periphery with an annular profile, and the grooves 332a may instead be cut into an outer surface of the deployment funnel 318a. The grooves 332a may, for example, permit fluid flow past the deployment funnel 318a from the intermediate tubular member lumen 152 and thus into the distal holding section 108 (FIG. 8). While a total of four grooves 332a are shown, equidistantly spaced apart around the periphery 320a, in some cases the deployment funnel 318a may include five, six or more distinct grooves 332a. In some cases, the deployment funnel 318 may instead only have one, two, or three distinct grooves 332a.

Figure 11E:
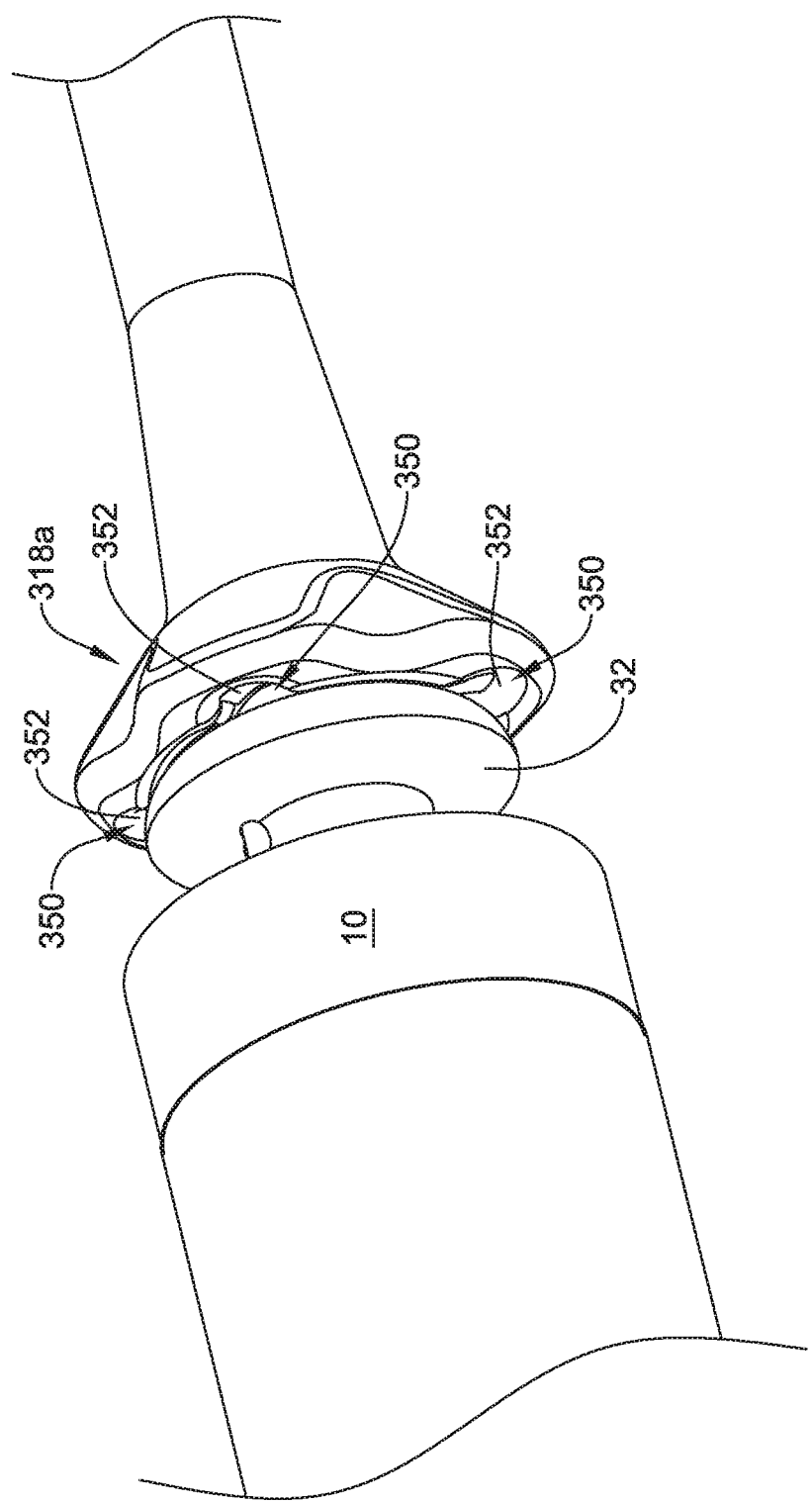
FIG. 11E is a perspective view of the deployment funnel of FIG. 11C engaged with an implantable device.

In some cases, it is possible that the presence of the implantable device 10 within the distal holding section 108 (FIG. 2) may potentially impact the flow of fluid passing beyond the deployment funnel 318a from the inner tubular member lumen 154 and into the distal holding section 108. In some cases, as illustrated, the deployment funnel 318a may include one or more recesses or grooves, such as curved notches 350, formed on a radially inwardly facing surface of the flared portion of the deployment funnel 318a that facilitate fluid flow through the deployment funnel 318a from the inner tubular member lumen 154 and past the head portion 32 of the docking member 30 of the implantable device 10 into the distal holding section 108. In some cases, each of the one or more recesses, grooves, or notches 350 may be considered as curved notches having a radially extending portion 352 and an axially extending portion 354. As illustrated in FIG. 11E, which shows the implantable device 10 in position with the head portion 32 of the docking member 30 seated against the radially inwardly facing surface of the flared portion of the deployment funnel 318a (as would occur inside the distal holding section 108), it can be seen that the radially extending portion 352 of each of the one or more curved notches 350 extend radially outward beyond the outer periphery of the head portion 32 of the docking member 30 extending proximally from the implantable device 10. The deployment funnel 318a may include one or more, or a plurality of recesses, grooves, or notches 350 formed on the radially inwardly facing surface to define one or more, or a plurality of fluid flow paths between the radially inwardly facing surface of the deployment funnel 318a and a surface of the head portion 32 of the docking member 30, for example. While a total of four recesses, grooves, or notches 350 are shown, equidistantly spaced apart, in some cases the deployment funnel 318a may include five, six or more recesses, grooves, or notches 350. In some cases, the deployment funnel 318a may instead only have one, two, or three recesses, grooves, or notches 350.

Figure 12:
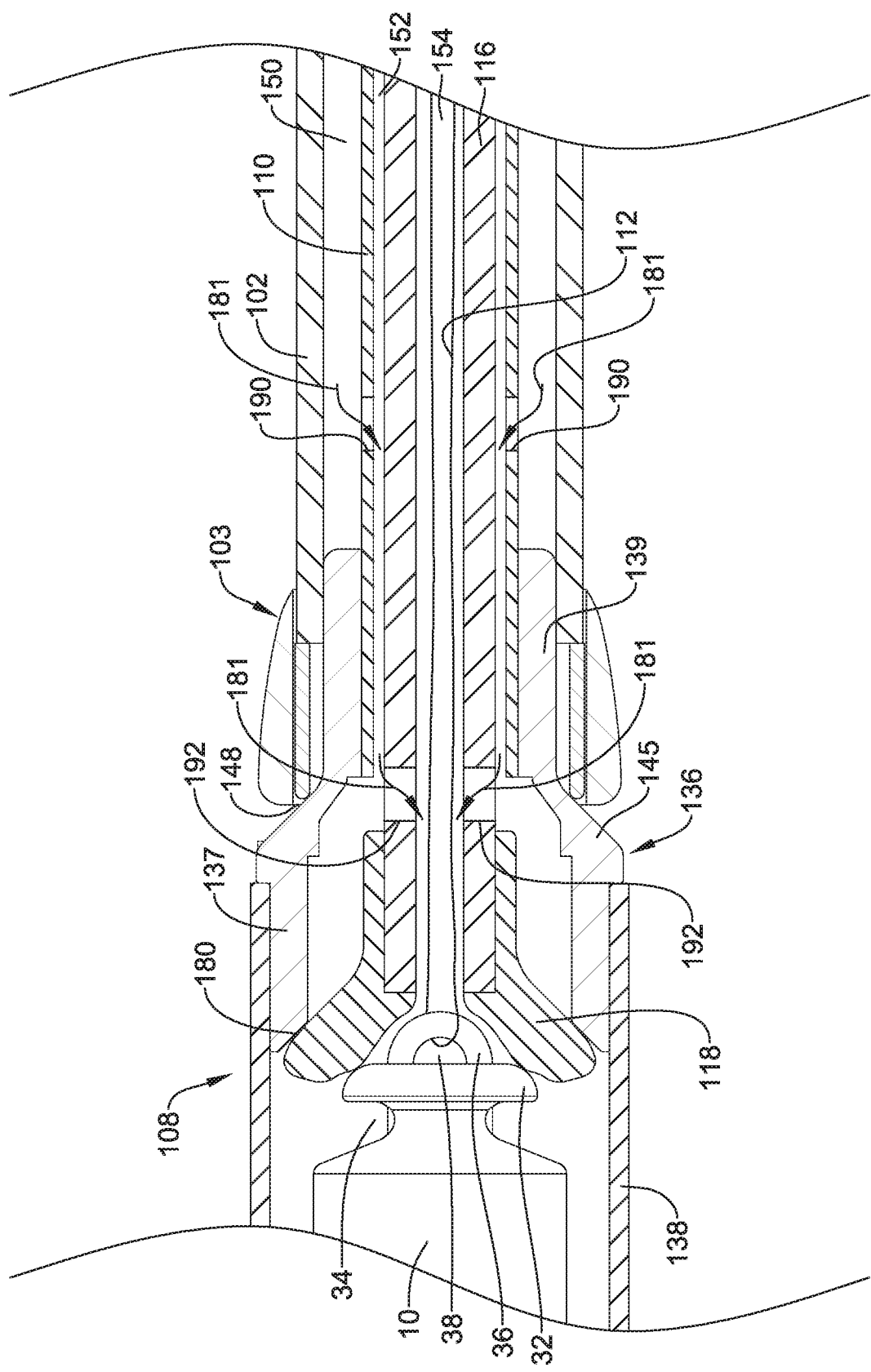
FIG. 12 is an enlarged partial cross-sectional view of an illustrative delivery device showing fluid paths through the delivery device.

FIG. 12 is a partial cross-sectional view showing the outer tubular member 102, the intermediate tubular member 110 and the inner tubular member 116 in a configuration that may, for example, be used for deploying the implantable device 10. As noted with respect to FIG. 4, the tether 112 extends distally through the inner tubular member lumen 154 and through the deployment funnel 118, and is coupled to the tether retention feature 36. For example, as shown in FIG. 12, the tether 112 passes through the opening 38 and thus around the tether retention structure 36 and extends proximally back through the inner tubular member lumen 154. It will be appreciated that the tether 112 does not interfere with fluid flow through the inner tubular member lumen 154.

As shown in FIG. 12, the deployment funnel 118 may not include features that enable fluid flow to pass the contact point 180. In some cases, the deployment funnel 118 may include one or more of the apertures, grooves and other features that permit fluid flow to pass the contact point 180. In some cases, the intermediate tubular member 110 may include one or more apertures 190 that enable fluid flowing through the outer tubular member lumen 150 to flow through the one or more apertures 190 from the outer tubular member lumen 150, indicated by arrows 181, and enter the intermediate tubular member lumen 152. The apertures 190 may extend through the annular sidewall of the intermediate tubular member 110, or the apertures may be formed at a joint between joined portions of the intermediate tubular member 110, such as at the junction between the intermediate tubular member 110 and the hub portion 136. In some cases, the inner tubular member 116 may include one or more apertures 192 that enable fluid flowing through the intermediate tubular member lumen 152 to flow through the one or more apertures 192, indicated by arrows 181, and enter the inner tubular member lumen 154. The apertures 192 may extend through the annular sidewall of the inner tubular member 116, or the apertures may be formed at a joint between joined portions of the inner tubular member 116, such as at the junction between the inner tubular member 116 and the deployment funnel 118. As a result, fluid flowing through the outer tubular member lumen 150 and/or fluid flowing through the intermediate tubular member lumen 152 may enter the inner tubular member lumen 154 proximate the distal holding section 108, and thus flow through and distally out of the deployment funnel 118 around the head portion 32 of the docking member 32 into the distal holding section 108. Thus, the outer tubular member lumen 150 and/or the intermediate tubular member lumen 152 may be flushed with fluid (e.g., saline) from the proximal end of the delivery device 100 (e.g., from one or more fluid ports in the handle assembly 120, with the fluid being expelled through the interior of the deployment funnel 118 into the distal holding section 108.

Figure 13:
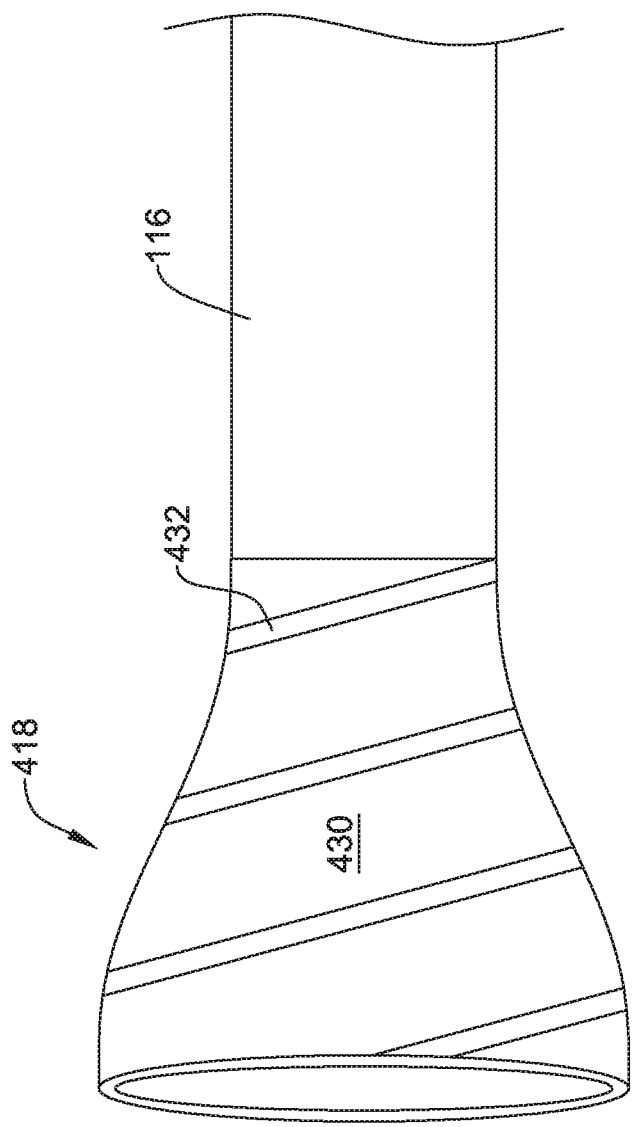
FIG. 13 is a plan view of a deployment funnel that can be used as a portion of the delivery devices of FIGS. 3, 10 and 12.

FIG. 13 is a side view of a deployment funnel 418 having an outer surface 430. In some cases, a helical groove 432 may be formed within the outer surface 430. While a total of three windings of the helical groove 432 are illustrated, it will be appreciated that in some cases the helical groove 432 may have a relatively tighter pitch, and thus would have more than three windings extending around the deployment funnel 418. In some cases, there may be a relationship between pitch (and hence number of windings) and the relative width and/or depth of the helical groove 418. For example, with a relatively large pitch (as illustrated), the helical groove 418 may be relatively larger (in width and/or depth) to accommodate fluid flow therethrough. Alternatively, with a smaller pitch, and hence a larger number of windings, the helical groove 418 may be relatively smaller (in width and/or depth) as there may effectively be a larger number of channels for fluid to flow past the deployment funnel 418 and into the distal holding section 108. It will be appreciated that the helical groove 432 may be formed as a left-handed or a right-handed helix.

FIGS. 9A, 9B, 11A, 11B, 11C, 11D, 11E, 12 and 13 show examples of deployment funnels that include structure to facilitate fluid flow past the deployment funnel. In some cases, the deployment funnel itself may be configured to permit fluid to flow through the deployment funnel. For example, in some cases the deployment funnel may be formed of a porous material. In some cases, the deployment funnel may be a polymeric structure having a plurality of micro-scale passages, holes and the like formed within the polymeric structure that enable fluid to flow through. In some cases, the deployment funnel may be formed of an open-celled foam, for example. In some cases, the deployment funnel may be formed of fused fibers. The deployment funnel may, for example, may be formed of woven or non-woven materials.

Figure 14:
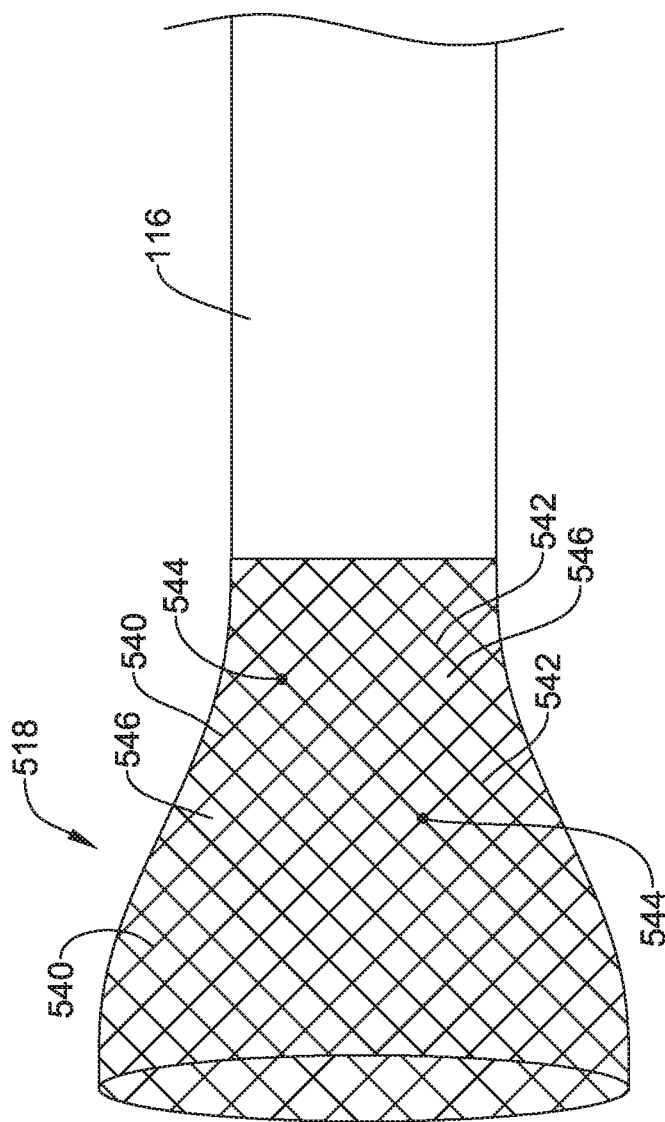
FIG. 14 is a plan view of a deployment funnel and inner tubular member that can be used as a portion of the delivery devices of FIGS. 3, 10 and 12.

FIG. 14 provides an example of a deployment funnel 518 having a lattice-like or mesh structure. In FIG. 14, the deployment funnel 518 may be seen as being braided, including a first plurality of windings 540 extending helically in a first direction and a second plurality of windings 542 extending helically in second direction different from the first direction such that the first plurality of windings 540 intersect the second plurality of windings 542 at a number of intersection points 544. In some cases, the intersection points 544 may be spaced relatively closer together, providing relatively smaller voids 546 defined by surrounding windings 540, 542. In some cases, the intersection points 544 may be spaced relatively farther apart, providing relatively larger voids 546 defined by surrounding windings 540, 542. It will be appreciated that the particular dimensions may be a function of desired fluid flow through the deployment funnel 518 relative to a desired mechanical strength of the deployment funnel 518.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL®400, NICKELVAC®400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A system for delivering an implantable leadless pacing device, the delivery device comprising:
   an elongate tubular member including a lumen extending therethrough;
   a distal holding section secured to and extending distally of a distal end of the elongate tubular member, the distal holding section defining a cavity therein and a distal opening;
   a deployment shaft slidingly disposed within the lumen of the elongate tubular member, the deployment shaft including a lumen extending therethrough;
   a deployment funnel secured to a distal end of the deployment shaft, the deployment funnel moveable longitudinally between a retracted position and an advanced position; and
   a leadless pacing device disposed in the cavity of the distal holding section with the deployment funnel in the retracted position, wherein the leadless pacing device includes a housing and a docking member extending proximally from the housing;
   wherein the deployment funnel is configured to permit fluid flow from the lumen of the deployment shaft into the cavity of the distal holding section when the deployment funnel is in the retracted position and the docking member of the leadless pacing device is seated against the deployment funnel.

2. The system of claim 1, wherein actuation of the deployment funnel from the retracted position to the advanced position advances the leadless pacing device from the distal opening of the distal holding section.

3. The system of claim 1, wherein the deployment funnel comprises one or more flow paths on a radially inwardly facing surface of the deployment funnel in order to permit fluid to flow past the docking member from the lumen of the deployment shaft in the retracted position.

4. The system of claim 3, wherein the one or more flow paths are recesses, grooves or notches.

5. The system of claim 1, wherein the deployment funnel is seated within a proximal portion of the distal holding section in the retracted position.

6. The system of claim 1, further comprising:
   a tether extending through the lumen of the deployment shaft; and
   a tether retention structure provided with the docking member;
   wherein the tether is engaged with the tether retention structure.

7. The system of claim 6, wherein the tether passes around the tether retention structure such that the tether includes first and second elongate portions extending proximal of the tether retention structure through the lumen of the deployment shaft alongside one another.

8. The system of claim 1, wherein the deployment funnel comprises one or more flow paths on a radially outwardly facing surface of the deployment funnel in order to permit fluid to flow past the docking member from the lumen of the elongate tubular member into the cavity of the distal holding section in the retracted position.

9. The system of claim 8, wherein a flared portion of the deployment funnel includes a fluted periphery defining the one or more flow paths on the radially outwardly facing surface of the deployment funnel.

10. A system for delivering an implantable leadless pacing device, the delivery device comprising:
    an elongate tubular member including a lumen extending therethrough;
    a distal holding section secured to and extending distally of a distal end of the elongate tubular member, the distal holding section defining a cavity therein and a distal opening;
    a deployment shaft slidingly disposed within the lumen of the elongate tubular member, the deployment shaft including a lumen extending therethrough;
    a deployment funnel secured to a distal end of the deployment shaft, the deployment funnel moveable longitudinally with longitudinal movement of the deployment shaft;
    a leadless pacing device disposed in the cavity of the distal holding section, wherein the leadless pacing device includes a housing and a docking member extending proximally from the housing, wherein the docking member is seated against a radially inwardly facing surface of the deployment funnel; and
    one or more fluid flow paths passing between the docking member and the radially inwardly facing surface of the deployment funnel to permit fluid to flow past the docking member from the lumen of the deployment shaft.

11. The system of claim 10, wherein the one or more flow paths are recesses, grooves or notches formed in the inwardly facing surface of the deployment funnel.

12. The system of claim 10, further comprising:
a tether extending through the lumen of the deployment shaft; and
a tether retention structure provided with the docking member;
wherein the tether is engaged with the tether retention structure.

13. The system of claim 12, wherein the tether passes around the tether retention structure such that the tether includes first and second elongate portions extending proximal of the tether retention structure through the lumen of the deployment shaft alongside one another.

14. The system of claim 10, wherein the deployment funnel comprises one or more flow paths on a radially outwardly facing surface of the deployment funnel in order to permit fluid to flow past the docking member from the lumen of the elongate tubular member into the cavity of the distal holding section.

15. The system of claim 14, wherein a flared portion of the deployment funnel includes a fluted periphery defining the one or more flow paths on the radially outwardly facing surface of the deployment funnel.

16. A method of delivering a leadless pacing device, comprising:
advancing a leadless pacing device through a vasculature of a patient with a delivery catheter, the leadless pacing device including a housing and a docking member extending proximally from the housing, the delivery catheter comprising:
an elongate tubular member including a lumen extending therethrough;
a distal holding section secured to and extending distally of a distal end of the elongate tubular member, the distal holding section defining a cavity therein and a distal opening;
a deployment shaft slidingly disposed within the lumen of the elongate tubular member, the deployment shaft including a lumen extending therethrough; and
a deployment funnel secured to a distal end of the deployment shaft, the deployment funnel moveable longitudinally between a retracted position and an advanced position;
the leadless pacing device being disposed in the cavity of the distal holding section with the docking member of the leadless pacing device seated against the deployment funnel in the retracted position;
providing a continuous supply of fluid through the lumen of the deployment shaft, wherein the fluid supplied through the lumen of the deployment shaft flows through one or more fluid flow paths passing between the docking member and a radially inwardly facing surface of the deployment funnel into the cavity of the distal holding section.

17. The method of claim 16, wherein the one or more flow paths are recesses, grooves or notches formed in the inwardly facing surface of the deployment funnel.

18. The method of claim 16, further comprising:
a tether extending through the lumen of the deployment shaft; and
a tether retention structure provided with the docking member;
wherein the tether is engaged with the tether retention structure.

19. The method of claim 18, wherein the tether passes around the tether retention structure such that the tether includes first and second elongate portions extending proximal of the tether retention structure through the lumen of the deployment shaft alongside one another.

20. The method of claim 16, further comprising:
moving the deployment funnel from the retracted position to the advanced position to deploy the leadless pacing device out of the distal opening.

* * * * *